United States Patent
Schuessler et al.

(10) Patent No.: US 11,648,104 B2
(45) Date of Patent: May 16, 2023

(54) IMPLANT IDENTIFICATION BY RADIOGRAPHIC MEANS

(71) Applicant: Allergan, Inc., Irvine, CA (US)

(72) Inventors: David J. Schuessler, Santa Ana, CA (US); Alberto Flores-Pujol, San Pablo (CR); Daniela Rodriguez-Estrada, Mercedes Norte (CR)

(73) Assignee: Allergan, Inc., North Chicago, IL (US)

( * ) Notice: Subject to any disclaimer, the term of this patent is extended or adjusted under 35 U.S.C. 154(b) by 0 days.

(21) Appl. No.: 16/870,819

(22) Filed: May 8, 2020

(65) Prior Publication Data

US 2020/0352704 A1 Nov. 12, 2020

Related U.S. Application Data (60) Provisional application No. 62/846,566, filed on May 10, 2019.

(51) Int. Cl.
*A61F 2/12* (2006.01)

(52) U.S. Cl.
CPC .......... *A61F 2/12* (2013.01); *A61F 2240/001* (2013.01); *A61F 2250/0098* (2013.01)

(58) Field of Classification Search
CPC ...... A61F 2/12; A61F 2/52; A61F 2250/0098; A61F 2240/001; A61B 2090/3937; A61B 90/39; A61B 90/90; A61B 90/94; A61L 31/18

See application file for complete search history.

(56) References Cited

U.S. PATENT DOCUMENTS

| | | | | |
|---|---|---|---|---|
| 4,863,470 | A | * 9/1989 | Carter | A61F 2/12 623/8 |
| 2012/0065500 | A1 | * 3/2012 | Rogers | A61L 31/18 600/431 |
| 2012/0065503 | A1 | 3/2012 | Rogers et al. | |
| 2015/0313708 | A1 | * 11/2015 | Mayo Martin | A61F 2/12 623/8 |
| 2016/0228716 | A1 | 8/2016 | Schmidt et al. | |

FOREIGN PATENT DOCUMENTS

| WO | WO 2007/025266 | 3/2007 |
|---|---|---|
| WO | WO 2017/196973 | 11/2017 |

* cited by examiner

*Primary Examiner* — Jennifer Dieterle
*Assistant Examiner* — Rebecca Lynee Zimmerman
(74) *Attorney, Agent, or Firm* — Stanek Lemon Crouse & Meeks, PA (57) ABSTRACT

A breast implant includes a flexible shell having an anterior face including an outer surface and an inner surface, and a marker attached to the inner surface of the anterior face of the shell. The marker includes a first layer of material having a radiopaque surface with readable characters for identifying a characteristic of the breast implant while in vivo, and a second layer of non-radiopaque material laminated onto the radiopaque surface. The readable characters defined by an outline formed from an absence of at least a portion of material of the radiopaque surface. The first layer of material with the readable characters is interposed between the inner surface of the anterior face of the shell and the second layer, and the readable characters are viewable in vivo using conventional imaging techniques.

22 Claims, 4 Drawing Sheets

IMPLANT IDENTIFICATION BY RADIOGRAPHIC MEANS

REFERENCE TO RELATED APPLICATIONS

This application claims priority to U.S. Provisional App. No. 62/846,566, filed on May 10, 2019, which is hereby incorporated by reference in its entirety.

TECHNICAL FIELD

The present disclosure relates generally to prosthetic implants, for example, mammary implants. More specifically, the present disclosure relates to a radiopaque identifier incorporated into a breast prosthesis, the marker being readable in vivo.

BACKGROUND

Implantable prostheses are commonly used to replace or augment body tissue. In the case of breast cancer, it is sometimes necessary to remove some or all of the mammary gland and surrounding tissue, which creates a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various areas of the body.

Tens of millions of women worldwide currently have breast implants with over a million more women undergoing surgery each year to receive new breast implants. Approximately 25% of implant surgeries are revision surgeries which are to replace existing implants with new implants. These revision surgeries typically occur years after the original implant date. The standard of practice to inform the patient as to their implant identification is to provide the patient and/or surgeon with a manufacturer-supplied card for them to retain which contains the implant information. However, these cards are easily misplaced and many women move or decide to see other implant surgeons. Therefore, most women do not know what brand or type or size implant that they have.

For revision surgery, identification of the current implant is important so that the revision surgery can be planned carefully and the correct style and size replacement implants can be ordered. With hundreds of different breast implants available, planning a precise breast revision surgery is very difficult for the surgeon if they do not know what implant was originally implanted. Having this implant identification is also important for executing or managing product alert or recall campaigns.

One attempt to address this issue has been made in some regions is to include an RFID tag within the breast implant that contains a unique numerical sequence. This RFID tag (e.g., Veriteq, Inc) can be read through the tissue by an appropriate close range RFID reader and the identification number can then be tracked through the RFID tag manufacturer's data base to reveal the implant manufacturer and the implant specifics. However, this method is expensive for the manufacturer to implement, requires special systems to create the number sequence traceability, requires an electronic component be incorporated in the implant, the user must have a specific RFID reader, and involves a third party intermediary that maintains the traceability of RFID number to the manufacturer.

SUMMARY

Accordingly, there is a need in the field for an implant identification marker which once the implant is situated in vivo, characters of the identification maker positioned on the implant are visible with most radiographic procedures, such as during a routine mammogram. This can eliminate the need to use specialized equipment to view the unique serialization and identification information of the implant.

In accordance with various embodiments of the present disclosure, a breast implant can include a flexible shell having an anterior face including an outer surface and an inner surface.

Further, a marker can be attached to the inner or outer surface of the anterior or a posterior face of the shell. The marker can include a first layer of material having a radiopaque surface with readable characters for identifying a characteristic of the breast implant while in vivo, and a second layer of non-radiopaque material laminated onto the radiopaque surface. The readable characters can be defined by at least one void in the material of the radiopaque surface. Such characters can be formed through a removal process.

The marker can also or alternatively be configured such that the first layer of material has radiopaque characters that are defined by the presence of radiopaque material on a surface. Such characters can be formed through an additive process.

The first layer of material with the readable characters can be interposed between the inner surface of the anterior face of the shell and the second layer, and the readable characters are viewable in vivo using conventional imaging techniques.

In some embodiments, a method of manufacturing a radiopaque identifier for a breast implant can include providing a first layer of material including a radiopaque material, attaching a second layer of non-radiopaque material to the first layer of material, and removing at least a portion of the radiopaque material to form the radiopaque identifier including readable characters defined by the removed portion of radiopaque material. The radiopaque material can be interposed between an outer surface of the first layer and the second layer. The readable characters can be viewable in vivo using X-ray imaging techniques.

In some embodiments, a method of manufacturing a breast implant can include forming a breast implant marker having readable characters for identifying a characteristic of the breast implant while in vivo, providing a shell having an anterior face, and attaching the breast implant marker to the anterior face of the shell.

The forming can include providing a first layer of material having an inner surface and an outer surface with a radiopaque material incorporated between the inner and outer surfaces, and attaching a second layer of non-radiopaque material to the inner surface of the first layer of material.

The forming can further include removing at least a portion of the radiopaque material from the first layer of material to form readable characters defined by absence of the portion of radiopaque material. The first layer of material having the readable characters can be interposed between the anterior face of the shell and the second layer of non-radiopaque material, and the readable characters can be viewable in vivo using conventional imaging techniques.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure provide a breast implant identification feature which incorporates a convenient and passive means for post-operative identification and traceability of the implant using common radiographic procedures like chest X-rays or routine mammography. The implant is provided with a radiographic marker (also referred to herein as an "identifier") that contains radiopaque material in the form of readable characters indicating a manufacturer's ID, catalog number, and/or implant serial number (UDI), so that when imaged with x-rays, the implant ID is human readable and traceable to the manufacturer's product history.

Most breast implants are marked directly with human readable information as to manufacturer, implant style, size and lot/serial number typically on a patch. During manufacturing, packaging, and at the time of implant or explant surgery, this information directly on the implant is very useful. In currently existing breast implants, these markings are typically done using laser or ink jet equipment by manufacturers to provide unique serialization and identification on the implant surface with traceability to the product history records. However, the currently existing markings are not human readable while the implant is in vivo.

The aforementioned configuration of the radiographic marker of the various embodiments described herein is advantageous in that implant size, shape, and any other particulars can be readily known to the patient and their current health care provider while the implant is in vivo. The present disclosure advantageously improves over the prior art in that the radiopaque marker or identifier, or at least the portion thereof contains that same information in a form that is human-readable while the implant is in vivo.

In accordance with some embodiments of the disclosure, manufacturing processes generally comprise forming a component of an implant assembly and integrating an identifier into the component, for example, a unique identifier, such as unique indicia specific to that particular component, during an early stage in the formation of the component. More specifically, the process may comprise forming a shell of a breast implant and labeling the shell with a unique identifier during molding of the shell. The identifier may comprise, for example, a serial number, bar code, indicia, or other form of identifier that contains that same information in a form that is human-readable and can be detectable while the implant is in vivo. Consequently, in some embodiments, the unique identifier becomes integrated into the shell of an assembled breast implant, thereby facilitating tracing of the specific shell.

In accordance with various embodiments of the present disclosure, a 5 mm wide strip of radiopaque material, for example 10% Barium Sulfate ($BaSO_4$) incorporated in silicone sheeting, is laminated to a non-radiopaque sheeting, for example clear silicone sheeting. The strip of radiopaque material is then controllably marked or etched with the desired information with a laser to remove only the radiopaque layer leaving a stenciled strip of human readable characters overlaying the non-radiopaque clear silicone sheeting. As shall be described in further detail below, a prototype gel-filled breast implant may be produced with a 10% BaSO$_4$ silicone strip attached to the inside of the shell. In some embodiments, the radiographic strip may be etched to include small rounded cut-outs of the BaSO$_4$ material to simulate logos or alpha-numeric characters in the radiopaque material.

The radiopaque strip marked with readable characters can now be incorporated into the breast implant by ordinary means of silicone vulcanization either inside the shell or on the exterior of the implant shell. As shall be described below, the radiopaque strip with the readable characters could also be placed between shell layers during the manufacturing of the shell. Further advantageously, in some embodiments, the radiopaque identifier strip may be placed down the midline of the anterior face of the shell so that it also acts as a visible and/or palpable orientation means during surgery especially for shaped implants. Also in this location on the anterior face there is less tissue to be scanned through so less imaging power is necessary when the ID information needs to be retrieved. The other advantage of this design where the radiopaque strip is down the implant midline is that it provides the surgeon with a means for determining if the implant is mal-positioned after surgery which is an issue that sometimes occurs with shaped breast implants.

In other embodiments, the present disclosure utilizes similar ink-jet or laser marking methods and implant grade radiopaque materials to produce human readable implant identification by radiographic means. For example, in some embodiments, the radiopaque material is provided as a component of a biocompatible ink and use implant serial number marking means similar to existing products with ink jet printing onto the orientation line. For example, tantalum powder, BaSO$_4$, palladium powder, or other high optical density materials could be incorporated into commonly available silicone inks to provide the radiopaque ID characters.

Once implanted the radiopaque strip or radiopaque characters are visible with most radiographic procedures that use X-rays. Radiographic equipment is readily available and does not need to be specialized for this application. As most women have regular mammograms, this is a convenient opportunity to retrieve implant information.

The various embodiments of manufacturing the unique identifier of the various embodiments of the present disclosure can be contrasted with conventional manufacturing processes which place identification information on preformed mandrel or mold, or pre-molded shells that are each part of a batch of such shells, each shell not being individually distinguished from each other. Such shells remain unlabeled and in storage for a significant time before each shell is removed from the batch and further processed to make an assembled implant.

Figure 1:
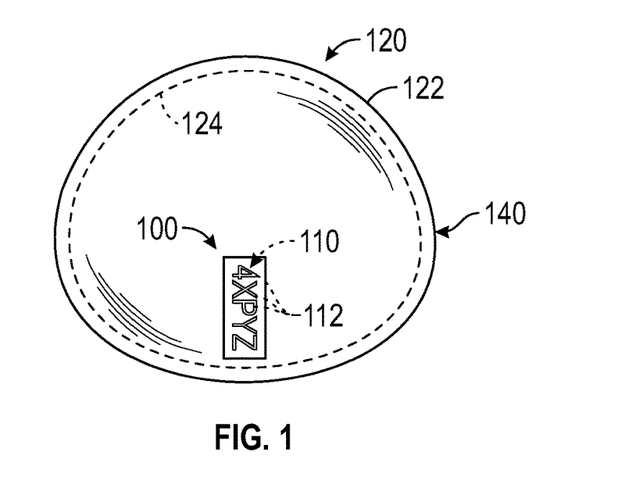
FIG. 1 is a perspective view of a breast implant shell having a radiographic marker, in accordance with some embodiments of the present disclosure.

FIG. 1 is a perspective view of a breast implant having a radiographic marker 100, in accordance with some embodiments of the present disclosure. According to various embodiments of the present disclosure, a shell 120 of the breast implant may be a flexible, elastomeric component that is typically dip-molded or rotational molded by applying a starter material, for example, an elastomeric material in a dispersion form, to a mandrel having the shape of the interior of a finished breast implant. The breast implant shell 120 may thus be formed having an anterior face 140 including an outer surface 122 and an inner surface 124, whereby the shape of the interior of the shell 120 is dictated by the shape of the mandrel used.

As illustrated in FIG. 1, the outer surface 122 may have an anatomical configuration matching that of a breast. Ultimately, the hollow interior of the shell 120 may be filled with an appropriate filler, for example, saline or silicone gel. In accordance with some embodiments, the shell 120 may be formed of a silicone gel. As depicted, the radiographic marker 100 may be in the form of a label or strip positioned within or on the shell 120. However, the various embodiments of the disclosure are not limited to the aforementioned configuration. For example, in some embodiments, the radiographic marker 100 may be formed in a circular, oval or similar shape. Although the radiographic marker 100 is illustrated as being positioned vertically in FIG. 1, the radiographic marker 100 may alternatively be placed horizontally for identification purposes. In accordance with some embodiments of the present disclosure, the radiographic marker 100 may be provided on at least one of the outer surface 122 or the inner surface 124 of the shell 120. In some embodiments, as illustrated in FIG. 1, the radiographic marker 100 may be positioned on the inner surface 124 of the anterior face 140 of the shell 120.

In some embodiments, the radiographic marker 100 may be placed on the mandrel prior to dipping or molding the implant or an additional layer of the implant. Thereafter, the implant can be formed using dip-molding or rotational molding. For example, the marker 100 can be attached to the mandrel and a first silicone coating or layer of the shell (that forms the inner surface 124) can be deposited onto the mandrel. Additional coatings or layers of the silicone may then be dip-molded or rotational molded over the first silicone coating or layer until forming the final silicone coating to create the outer surface 122.

Further, in some embodiments, the radiographic marker 100 may be positioned between the inner and outer surfaces 124 and 122 of the breast implant shell 120. For example, the radiographic marker 100 may be positioned on the shell 120 between dippings which form multiple layers of the shell 120 between the inner and outer surfaces 124 and 122, such that the unique identifier is located between such layers which are interposed between the inner and outer surfaces 133 and 124 of the shell 120.

Figure 2:
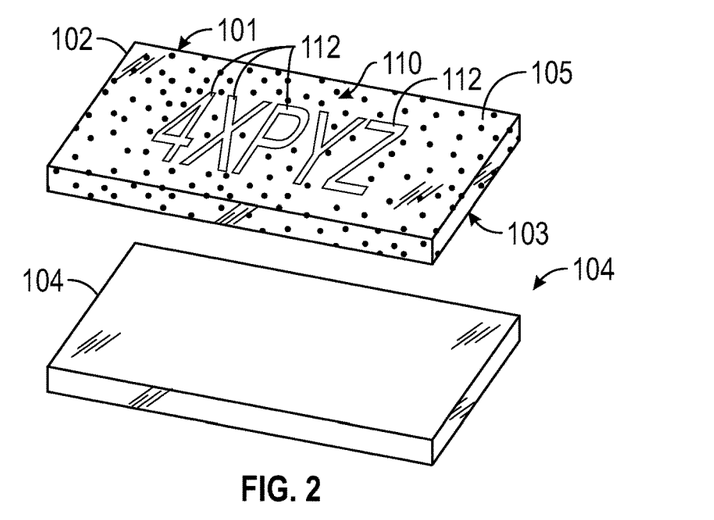
FIG. 2 is an exploded view of the radiographic marker of FIG. 1, in accordance with some embodiments of the present disclosure.

FIG. 2 is an exploded view of the radiographic marker of FIG. 1, in accordance with some embodiments of the present disclosure. As depicted, the radiographic marker 100 may include a first layer 102 incorporating a radiopaque material 105 therein and a second layer 104, for example, a non-radiopaque second layer, coupled to the first layer 102. The first layer 102 may include an outer surface 101 and an inner surface 103 opposing the outer surface 101, and the second layer 104 may be coupled to and positioned over the inner surface 103 of the first layer 102. As depicted in FIG. 2, the radiopaque layer 102 may include a radiopaque identifier 110 that contains the radiopaque material 105 in the form of readable characters 112. In FIG. 2, the readable characters 112 are illustrated in the form of a combination of numbers and letters "4XPYZ." However, any conceivable combination of numbers, letters, and/or symbols may be used as the readable characters 112. In some embodiments, the readable characters 112 of the radiopaque identifier 110 may be defined on the first layer 102 as an outline created by absence of at least a portion of the radiopaque material 105.

For example, the absence of at least a portion of the radiographic material may include at least one void, gap, hole, opening, space, or discontinuity in the continuous surface of the radiopaque material 105. As such, in some embodiments, the at least one void, gap, hole, opening, space, or discontinuity may be formed by laser etching the continuous surface of the radiopaque material 105 to create the absence of material defined by the at least one void, gap, hole, opening, space, or discontinuity in the continuous surface of the radiopaque material 105. However, the various embodiments discussed herein are not limited to laser etching, but may otherwise be performed using any other suitable material removal or material additive processes. For example, in some embodiments, the readable characters 112 of the radiopaque identifier 110 may be formed using additive manufacturing processes such as 3D printing. Accordingly, the at least one void, gap, hole, opening, space, or discontinuity may define an outline, stencil, contour, sketch, tracing, or silhouette of readable characters in the continuous surface of the radiopaque material 105.

The readable characters 112 may be textual characters, alpha-numeric characters, numeric characters, or other symbols in the form of numbers, acronyms, or other words readily identifiable to the practitioner. In some embodiments, the readable characters 112 may correspond to or otherwise signify important identification information about the implant 120 including, but not limited to size, shape, surface texture, position/orientation, and other relevant information about the implant manufacturer's product history. For example, the readable characters 112 of the radiopaque identifier 110 may be in the form of a manufacturer's ID and/or an implant serial number (UDI) which can be used to easily retrieve various other important information about the implant which is necessary for correct replacement of the implant during revision surgeries.

In accordance with some embodiments, because the material forming the outline of the radiopaque identifier 110 is radiopaque, the readable characters 112 permit the radiopaque identifier 110 to be viewable in vivo when exposed to a radiographic source of energy. For example, once implanted the radiopaque strip or radiopaque characters 112 are visible with most radiographic procedures that use X-rays. Advantageously, the radiopaque identifier 110 is viewable using routine radiographic equipment that is readily available and does not need to be specialized for this application. As most women have regular mammograms, this is a convenient opportunity to retrieve implant information without having to employ more complicated, costly, and time consuming equipment such as the aforementioned RFID technology which is conventionally used to retrieve information relating to the implant.

As discussed above, the first layer 102 may incorporate a radiopaque material 105 therein. In particular, the first layer 102 may be formed of a clear material, e.g., a clear silicone material with the radiopaque material 105 dispersed therein. For example, the first layer 102 may be formed of a clear silicone sheeting with particles of the radioactive material 105 dispersed therein. In some embodiments, the radiopaque material 105 may be, but is not limited to, barium sulfate. For example, the first layer 102 may be formed from silicone sheeting having particles of barium sulfate dispersed therein. In some embodiments, the barium sulfate ($BaSO_4$) may be dispersed in the silicone sheeting of the first layer 102 in a concentration of about 10% by weight. The concentration of the barium sulfate or other radiopaque material present in the silicone sheeting may vary based on its radiographic density, the imaging resolution needed, the location and distance of the marker relative to the skin surface, or imaging equipment. In general, and in the case of barium sulfate, the concentration can range from as low as about 1% to about 20% or more, such as about 30%, about 40%, or about 50%, or at least about 1%, at least about 5%, at least about 10%, at least about 15%, at least about 20%, at least about 25%, at least about 30%, at least about 35%, at least about 40%, or at least about 50%. For example, in some embodiments, the concentration of the $BaSO_4$ in the first layer 102 may range from about 1% to about 20%, from about 5% to about 15%, from about 7.5% to about 12.5%, or in some cases approximately 10% by weight. In some embodiments, the concentration of the $BaSO_4$ in the first layer 102 may range from about 1% to about 90%, from about 10% to about 80%, from about 20% to about 70%, from about 30% to about 60%, or from about 40% to about 50% by weight. Though recited in terms of certain ranges, it will be understood that all ranges from the lowest of the lower limits to the highest of the upper limits are included, including all intermediate ranges or specific dimensions.

In other embodiments, the first layer 102 may incorporate a strip of the radiopaque material, e.g., $BaSO_4$ therein having a same thickness as the first layer 102 itself. In these embodiments, the strip of radiopaque material may extend from the outer surface 101 to the inner surface 103 of the first layer 102.

In accordance with various embodiments of the present disclosure, the first layer 102, having the radiopaque material 105 incorporated therein, may be attached or otherwise coupled to the second layer 104. The second layer 104 may be may be formed of a clear material, e.g., a clear silicone material without a radiopaque material 105 incorporated therein. In some embodiments, the first layer 102 having the radiopaque material 105 therein is laminated to the second layer 104 in order to form the radiographic marker 100. The second layer 104 may thus form a backing for the first layer 102 and advantageously provide additional stiffness or rigidity. After the first layer 102 is laminated to the second layer 104, the joined layers 102 and 104 may be cut into a strip or other shape in preparation to form the radiopaque identifier 110.

Figure 3A:
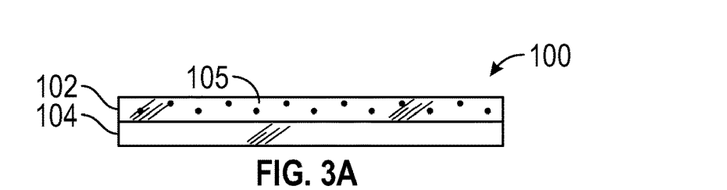
FIG. 3A is a side view of the radiographic marker of FIG. 1, in accordance with some embodiments of the present disclosure.
Figure 3B:
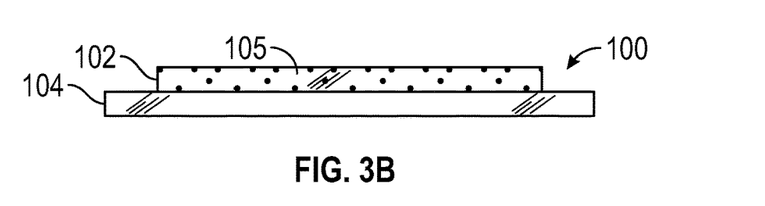
FIG. 3B is a side view of a radiographic marker, in accordance with some embodiments of the present disclosure.

FIG. 3A is a side view of the radiographic marker of FIG. 1, in accordance with some embodiments of the present disclosure. FIG. 3B is a side view of a radiographic marker, in accordance with some embodiments of the present disclosure. As previously described, once the first layer 102 is laminated to the second layer 104, the joined layers 102 and 104 maybe cut into the shape of a strip in preparation to form the radiopaque identifier 110. As depicted in FIG. 3A, the first and second layers 102 and 104 may be cut or otherwise formed with a same length and width so that the first layer 102 lies directly above the second layer 104 with no overlap. Alternatively, as depicted in FIG. 3B, in some embodiments, the second layer 104 may be larger in size than the first layer 102. For example, the second (non-radiopaque) layer 104 may be greater in length and/or width, such that a portion of the second (non-radiopaque) layer 104 overlaps the boundary of the radiopaque layer 102. The aforementioned configuration may be advantageous over that where the first and second layers 102 and 104 are of the same size, as the configuration in which the second layer 104 is larger than the first layer 102 provides extra surface area of the second layer 104 for bonding to the surface of the breast implant 120. Accordingly, the radiographic marker 100 may be more securely adhered, coupled, or otherwise integrated on the breast implant 100. In some embodiments of the present disclosure, the thicknesses of the first and second layers 102 and 104 may be equal. However, in other embodiments, the thickness of the second layer 104 may be greater than that of the first layer 102, so as to provide a firmer and/or more rigid support layer or backing to the first layer 102. In other embodiments, however, the first layer 102 may be thicker than the second layer 102 so as to provide sufficient thickness of the readable characters 112 to be etched out of the first layer 102 to form the radiopaque identifier 110.

Figure 4:
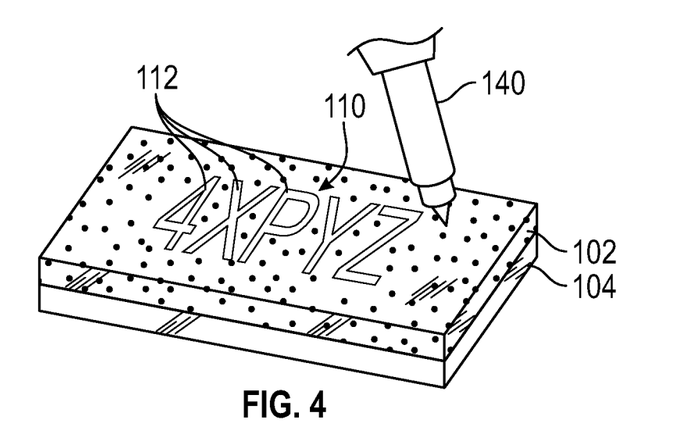
FIG. 4 is a perspective view demonstrating how readable characters are etched into the radiographic marker, in accordance with some embodiments of the present disclosure.

FIG. 4 is a perspective view demonstrating how readable characters are etched into the radiographic marker, in accordance with some embodiments of the present disclosure. As discussed above, the radiographic marker 100 may include the radiopaque identifier 110 in the form of readable characters 112. In particular, as briefly discussed above, the readable characters 112 of the radiopaque identifier 110 may be formed on the radiopaque layer 102. In particular, in some embodiments, as illustrated in FIG. 4, the readable characters 112 of the radiopaque identifier 110 may be formed on the first layer 102 as an outline created by absence of at least a portion of the radiopaque material 105. In some embodiments, the readable characters 112 of the radiopaque identifier 110 may be formed by removal of at least a portion of the first layer 102. For example, the readable characters 112 of the radiopaque identifier 110 may be formed by using a laser 140 to controllably remove or etch out the radiopaque material to create an outline of readable characters, for example in the form of a stencil.

The readable characters 112 may correspond to or otherwise signify important identification information about the implant 120 including, but not limited to size, shape, surface texture, position/orientation, and other relevant information about the implant manufacturer's product history. For example, the readable characters 112 of the radiopaque identifier 110 may be in the form of a manufacturer's ID and/or an implant serial number (UDI) which can be used to easily retrieve various other important information about the implant which is necessary for correct replacement of the implant during revision surgeries.

As depicted in FIG. 4, the radiographic marker 100 may be controllably marked or etched with the desired information with the laser 140 to remove only portions of the radiopaque layer 102, thereby leaving a stenciled strip of human readable characters overlaying the non-radiopaque clear silicone sheeting. As such, the non-radiopaque second layer 104 remains intact as a backing and forms the surface against which the radiopaque layer 102 may be contrasted against in order to view the readable characters 112. For example, in some embodiments, the laser 140 may be used to controllably etch out portions of the radiopaque layer 102 to form the outline of the readable characters 112. In some embodiments, the radiopaque layer 102 may be etched to include small rounded cut-outs of the BaSO$_4$ material to simulate logos or alpha-numeric characters in the radiopaque material.

The readable characters 112 of the radiopaque identifier 110 may include one or more alphanumeric or other characters, predefined symbols and/or arbitrary symbols. In some embodiments, as described herein, readable characters 112 of the radiopaque identifier 110 may be designed to project a negative image when viewed by the X-ray imaging technology. In other embodiments however, the readable characters 112 of the radiopaque identifier 110 may be adapted to provide a positive image when detected by the X-ray imaging technology.

Figure 5A:
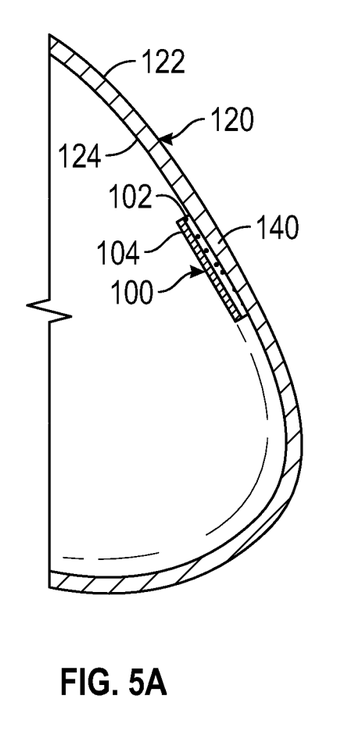
FIG. 5A is a cross-sectional side view of the breast implant shell of FIG. 1 having the radiographic marker of FIG. 3A, in accordance with some embodiments of the present disclosure.
Figure 5B:
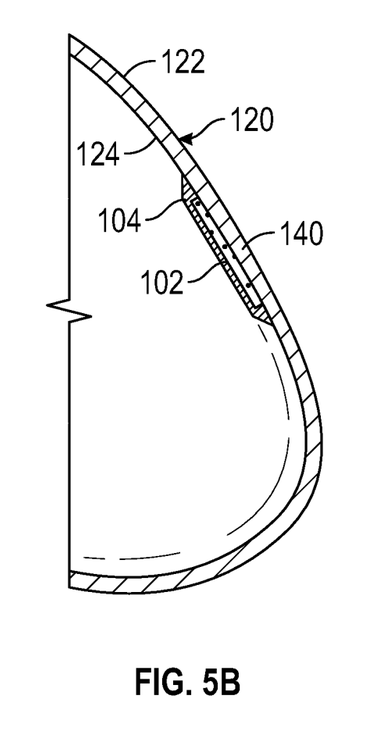
FIG. 5B is a cross-sectional side view of the breast implant shell of FIG. 1 having the radiographic marker of FIG. 3B, in accordance with some embodiments of the present disclosure.

FIG. 5A is a cross-sectional side view of the breast implant shell of FIG. 1 having the radiographic marker of FIG. 3A, in accordance with some embodiments of the present disclosure. FIG. 5B is a cross-sectional side view of the breast implant shell of FIG. 1 having the radiographic marker of FIG. 3B, in accordance with some embodiments of the present disclosure.

In some embodiments, after the readable characters 112 have been laser etched into the radiopaque layer 102, the radiographic marker with the readable characters 112 may be incorporated onto or into the breast implant shell 120. As depicted in FIGS. 5A and 5B, the breast implant shell 120 may be produced with the BaSO$_4$ silicone radiographic marker 100 attached to the inner surface 124 of the anterior face 140 of the shell 120. In some embodiments, the radiographic strip may be etched to include small rounded cut-outs of the BaSO$_4$ material to simulate logos or alpha-numeric characters in the radiopaque material.

As depicted illustrated in FIGS. 5A and 5B, the radiographic marker 100 is attached to the inner surface 124 of the anterior face of the shell 120. However, the various embodiments of the present disclosure are not limited to the aforementioned configuration. In other embodiments the radiographic marker 100 may be incorporated within layers of the shell 120 interposed between the inner and outer surfaces 124 and 122 of the shell 120. For example, the radiographic marker 100 may be positioned between the inner and outer surfaces 124 and 122 of the anterior face of the shell 120. Since the material forming the implant shell 120 is typically radiolucent, for example, silicone, the radiopaque characters 112 of the marker 100 may be viewed through the various shell layers when subjected to X-ray radiation.

The radiographic marker 100 may be attached to the shell 120 by any ordinary or suitable means. In accordance with some embodiments of the present disclosure, the radiographic marker may be attached or otherwise integrated onto or into the shell 120 by silicone vulcanization. However, the various embodiments of the present disclosure are not limited to the aforementioned configuration. For example, the radiographic marker may be adhered to, molded into, embedded within, or otherwise affixed to the implant shell 120. Additionally, in some embodiments, the radiopaque marker 100 may not be fixed directly to the shell, but may still be positioned directly adjacent to the shell 120 and held in position by curing the silicone gel filler around the radiographic marker 100.

In accordance with some embodiments, because the material forming the outline of the radiopaque identifier 110 is radiopaque or radiolucent, the readable characters 112 permit the radiopaque identifier 110 to be viewable in vivo when exposed to a radiographic source of energy. For example, once implanted the radiopaque strip or radiopaque characters 112 are visible with most radiographic procedures that use X-rays. Advantageously, the radiopaque identifier 110 is viewable using routine radiographic (in particular X-ray) equipment that is readily available and does not need to be specialized for this application. As most women have regular mammograms, this is a convenient opportunity to retrieve implant information without having to employ more complicated, costly, and time consuming equipment such as the aforementioned RFID technologies which are conventionally used to retrieve information relating to the implant.

Figure 6:
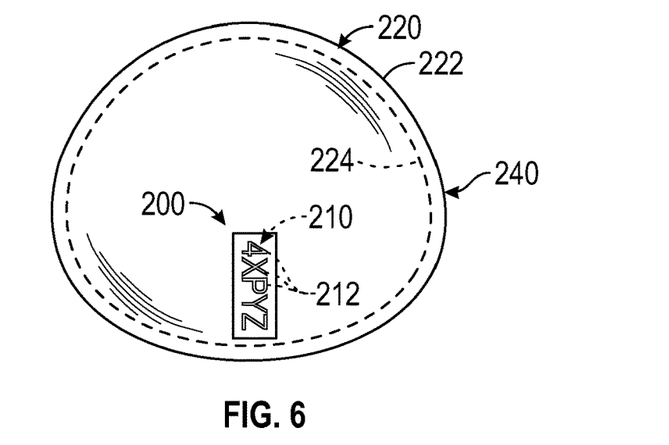
FIG. 6 is a perspective view of a breast implant shell having a radiographic marker, in accordance with some embodiments of the present disclosure.

FIG. 6 is a perspective view of a breast implant shell 220 having a radiographic marker 200, in accordance with some embodiments of the present disclosure. According to various embodiments of the present disclosure, the breast implant shell 220 may be similar to the breast implant shell 120 described above with respect to FIG. 1. In particular, the breast implant shell 220 may be a flexible, elastomeric component that may be dip-molded or rotational molded by applying a starter material, for example, an elastomeric material to a mandrel having the shape of the interior of a finished breast implant. The breast implant shell 220 may thus be formed with an anterior face 240 having an outer surface 222 and an inner surface 224, whereby the shape of the interior of the shell 220 is dictated by the shape of the mandrel used.

As illustrated in FIG. 6, the outer surface 222 may have an anatomical configuration and shape matching that of a breast. Ultimately the hollow interior of the shell 220 may be filled with an appropriate silicone gel.

As depicted in FIG. 6, the radiographic marker 200 may be in the form of a strip or label provided within or on the shell 220. For instance, the radiographic marker 200 may be attached to a surface of the shell 220. In some embodiments, the radiographic marker 200 may be formed in a circular, oval or similar shape. Although the radiographic marker 200 is illustrated as being positioned vertically in FIG. 6, the radiographic marker 200 may alternatively be placed horizontally for identification purposes. In accordance with some embodiments of the present disclosure, the radiographic marker 200 may be provided on at least one of the outer shell surface 222 or the inner shell surface 224. In some embodiments, as illustrated in FIG. 6, the radiographic marker 200 may be positioned on the inner surface 224 of the anterior face 240 of the shell 220. In other embodiments, the radiographic marker 200 may be positioned between the inner and outer surfaces 224 and 222 of the breast implant shell 220. For example, the radiographic marker 200 may be positioned on the shell 220 between dippings which form multiple layers of the shell. The multiple layers of the shell may be interposed between the inner and outer surfaces 224 and 222 of the shell 220 such that the radiographic marker 100 is located between such layers.

Figure 7:
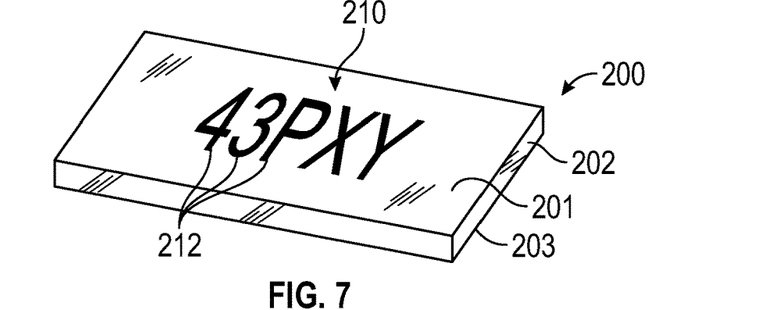
FIG. 7 is a view of the radiographic marker of FIG. 6, in accordance with some embodiments of the present disclosure.

FIG. 7 is an exploded view of the radiographic marker of FIG. 6, in accordance with some embodiments of the present disclosure. According to various embodiments of the present disclosure, the radiographic marker 200 may include a single layer or body 202 incorporating a radiopaque material therein. The body 202 may include an outer surface 201 and an inner surface 203 disposed opposite to the outer surface 201. As depicted in FIG. 7, the body 102 may be a radiopaque layer including a radiopaque identifier 210 that contains the radiopaque material in the form of readable characters 212. In the illustrated embodiments, the radiopaque material forming the radiopaque identifier 210 may be a radiopaque ink. For example, in some embodiments, the radiopaque identifier 210 may be formed of a bio-compatible ink incorporating a radiographic material therein. In some embodiments, the bio-compatible ink may be a silicone ink, and the radiopaque material may be tantalum powder, BaSO₄, palladium powder, or any other high optical density materials capable of being incorporated into a bio-compatible in. The readable characters 212 of the radiopaque identifier 210 may be written or otherwise printed on the body of the radiographic marker. Similar to the embodiments of FIG. 1, the readable characters 212 of the radiopaque identifier 210 may correspond to or otherwise signify important identification information about the implant 220 including, but not limited to size, shape, surface texture, position/orientation, and other relevant information about the implant manufacturer's product history. For example, the readable characters 212 of the radiopaque identifier 210 may be in the form of a manufacturer's ID and/or an implant serial number (UDI) which can be used to easily retrieve various other important information about the implant which is necessary for correct replacement of the implant during revision surgeries.

In accordance with some embodiments, because the material forming the outline of the radiopaque identifier 210 is radiopaque, the readable characters 212 permit the radiopaque identifier 210 to be viewable in vivo when exposed to a radiographic source of energy. For example, once implanted the radiopaque readable characters 212 are visible with most radiographic procedures that use X-rays. Advantageously, the radiopaque identifier 210 is viewable using routine radiographic equipment that is readily available and does not need to be specialized for this application. As most women have regular mammograms, this is a convenient opportunity to retrieve implant information without having to employ more complicated, costly, and time consuming equipment such as the aforementioned RFID or MRI technologies which are conventionally used to retrieve information relating to the implant.

Figure 8:
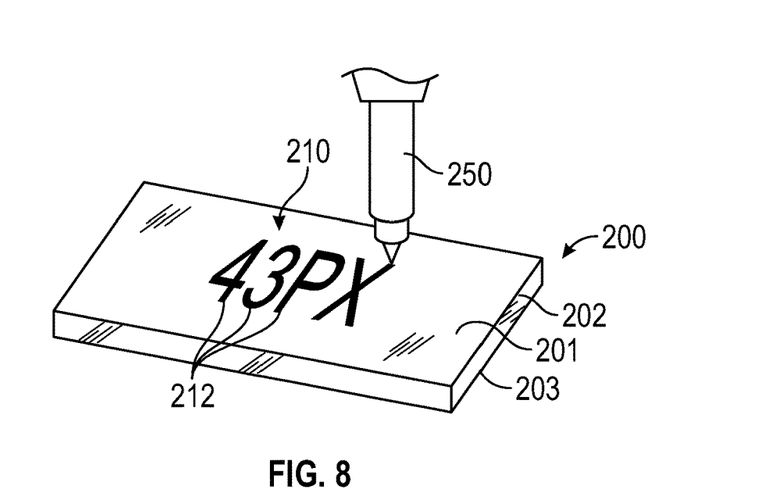
FIG. 8 is a perspective view demonstrating how readable characters are written onto the radiographic marker, in accordance with some embodiments of the present disclosure.

FIG. 8 is a perspective view demonstrating how readable characters are written onto the radiographic marker 200, in accordance with some embodiments of the present disclosure. As discussed above, the radiographic marker 200 may include the radiopaque identifier 210 in the form of readable characters 212. In particular, as briefly discussed above, the readable characters 212 of the radiopaque identifier 210 may be written on the radiopaque layer 102.

As discussed above, the radiopaque identifier 210 may be written or otherwise printed on the outer surface 201 of the radiographic marker 200. In particular, the body 202 may be formed as a strip of a clear material, e.g., a clear silicone strip with the radiopaque identifier 210 written or printer thereon. In some embodiments, the radiopaque identifier 210 may be printed on the clear silicone body 102 of the radiographic marker 200 by a suitable printing technique, such as, for example, ink-jet printing. In these embodiments, as illustrated in FIG. 8, an ink jet printer 250 may be used to write or print the readable characters 212 of the radiopaque identifier 210 on the outer surface 201 of the radiographic marker 200. However, the various embodiments of the present disclosure are not limited to the aforementioned printing method, and may also include, but not be limited to, for example engraving, mono-type, offset, cliché transfer, gliceé printing, or any other suitable additive manufacturing method, for example 3D printing.

In accordance with some embodiments, the readable characters 212 of the radiopaque identifier 210 may we directly written or printed on the anterior face 240 of the shell 220. The specific shell or assembly identification information, such as part number, lot number, size, style, manufacturer, etc., could all be directly written on the inner surface 224 or the outer surface 222 of the anterior face 240 of the shell 220.

Similar to the embodiments of FIG. 1, the readable characters 212 of the radiopaque identifier 210 may correspond to or otherwise signify important identification information about the implant 220 including, but not limited to size, shape, surface texture, position/orientation, and other relevant information about the implant manufacturer's product history. For example, the readable characters 212 of the radiopaque identifier 210 may be in the form of a manufacturer's ID and/or an implant serial number (UDI) which can be used to easily retrieve various other important information about the implant which is necessary for correct replacement of the implant during revision surgeries. The readable characters 212 of the radiopaque identifier 210 may include one or more alphanumeric or other characters, predefined symbols and/or arbitrary symbols. In some embodiments, as described herein, the readable characters 212 of the radiopaque identifier 110 may be adapted to provide a positive image when detected by the X-ray imaging technology.

The aforementioned configurations of the radiographic markers 100 and 200 of the various embodiments described herein eliminate the need to have to store important information about the implant on a card which may easily become lost or misplaced over the years, leaving the patient having to guess what kind of implant was originally used.

Figure 9:
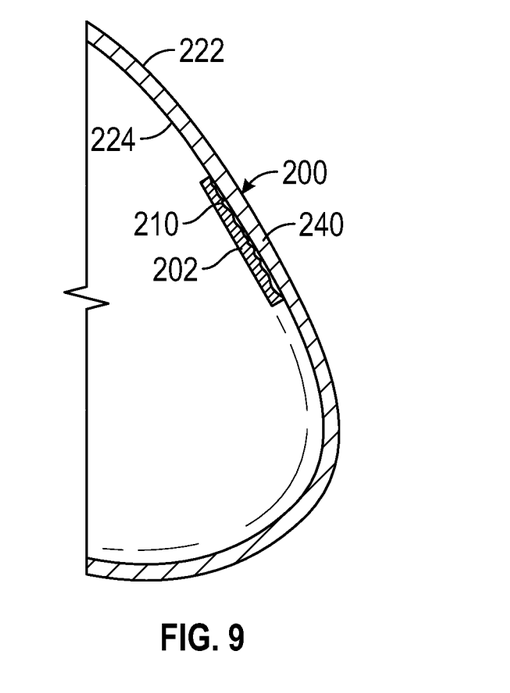
FIG. 9 is a cross-sectional side view of the breast implant shell of FIG. 6 having the radiographic marker of FIG. 7, in accordance with some embodiments of the present disclosure.

FIG. 9 is a cross-sectional side view of the breast implant shell of FIG. 6 having the radiographic marker of FIG. 7, in accordance with some embodiments of the present disclosure. FIG. 5B is a cross-sectional side view of the breast implant of FIG. 1 having the radiographic marker of FIG. 3B, in accordance with some embodiments of the present disclosure.

In some embodiments, after the readable characters 212 have been written or printed onto the body 102, the radiographic marker 210 with the readable characters 212 may be incorporated onto or into the breast implant shell 220. As depicted in FIG. 9, the breast implant shell 220 may be produced with the BaSO$_4$ silicone radiographic marker 200 attached to the inner surface 224 of the anterior face 240 of the shell 220. As depicted illustrated in FIG. 9, the radiographic marker 200 is attached to the inner surface 224 of the anterior face 240 of the shell 220. However, the various embodiments of the present disclosure are not limited to the aforementioned configuration. In other embodiments the radiographic marker 200 may be incorporated within layers of the shell 220. For example, similar to the radiographic marker 100, the radiographic marker 200 may be interposed, encapsulated, sandwiched, layered, or otherwise positioned between layers interposed between the inner and outer surfaces 224 and 222 of the anterior face 240 of the shell 220. Since the material forming the implant shell 220 is typically radiolucent, for example, silicone, the radiopaque characters 212 of the radiographic marker 200 may be viewed through the shell layers when subjected to X-ray radiation.

Similar to the radiographic marker 100 of the embodiments of FIG. 1, the radiographic marker 200 may be attached to the shell 220 by any ordinary or suitable means. In accordance with some embodiments of the present disclosure, the radiographic marker 200 may be attached or otherwise integrated onto or into the shell 220 by silicone vulcanization. However, the various embodiments of the present disclosure are not limited to the aforementioned configuration. For example, the radiographic marker may be adhered to, molded into, embedded within, or otherwise affixed to the implant shell 220.

In accordance with some embodiments, because the ink forming the radiopaque identifier 210 is radiopaque, the readable characters 212 permit the radiopaque identifier 210 to be viewable in vivo when exposed to a radiographic source of energy. For example, once implanted the radiopaque strip or radiopaque characters 212 are visible with most radiographic procedures that use X-rays. Advantageously, the radiopaque identifier 210 is viewable using routine radiographic equipment that is readily available and does not need to be specialized for this application. As most women have regular mammograms, this is a convenient opportunity to retrieve implant information without having to employ more complicated, costly, and time consuming equipment such as the aforementioned RFID technology which is conventionally used to retrieve information relating to the implant.

Figure 10A:
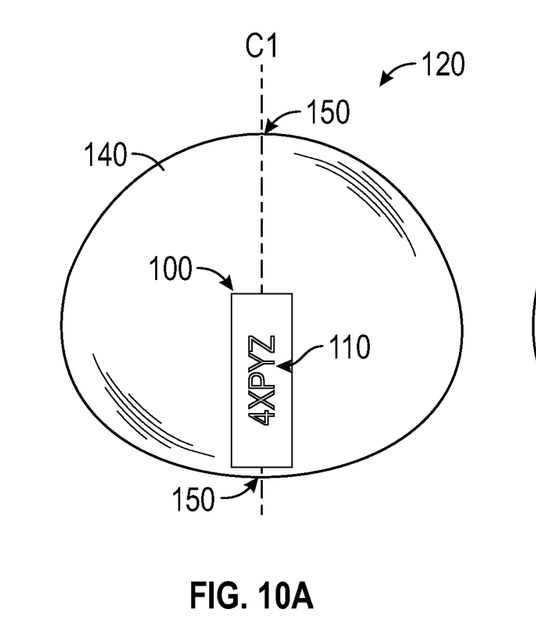
FIG. 10A is a front view of a shaped breast implant having the radiographic marker of FIG. 2 positioned as an orientation line, in accordance with some embodiments of the present disclosure.
Figure 10B:
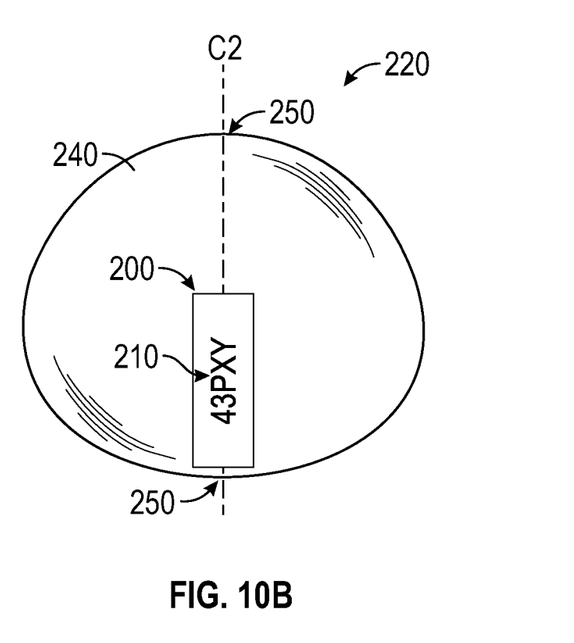
FIG. 10B is a front view of a shaped breast having the radiographic marker of FIG. 7 positioned as an orientation line, in accordance with some embodiments of the present disclosure.

FIG. 10A is a front view of a shaped breast implant having the radiographic marker of FIG. 2 positioned as an orientation line, in accordance with some embodiments of the present disclosure. FIG. 10B is a front view of a shaped breast having the radiographic marker of FIG. 7 positioned as an orientation line, in accordance with some embodiments of the present disclosure. In accordance with various embodiments of the present disclosure, the radiographic marker 100, 200 may be shaped in the form of a straight line or strip, and positioned on a respective anterior faces 140 and 240 of the respective shells 120 and 220. In some embodiments, each of the anterior faces 140 and 240 may further include a respective upper pole region 150 and 250, and a respective lower pole region 155 and 255. In accordance with various embodiments, a midline C1, C2, of each of the flexible shells 120 and 220 extends from the respective upper pole region 150, 250 to the lower pole region 155, 255.

Advantageously, the radiographic markers 100 and 200 may each be positioned on the respective midlines C1, C2, of the anterior faces 140, 240 of the respective shells 120, 220 so that as to act as a visible and/or palpable orientation means during surgery especially for shaped implants. In some embodiments, the radiographic markers 100 and 200 may be attached to either of the inner surfaces 124 and 224 or the outer surfaces 122 and 222 of the respective shells 120 and 220. For example, the radiographic markers 100 and 200 may be silicone vulcanized to either of the inner surfaces 124 and 224 or the outer surfaces 122 and 222 of the respective shells 120 and 220. Further advantageously, in these locations on the anterior faces 140 and 240 there is less tissue to be scanned through (than for example a posterior face of the shell) in order to detect the radiopaque identifier 110, 210, therefore less imaging power is necessary when the ID information associated with the radiopaque identifier 110, 210 needs to be retrieved. An added advantage of the aforementioned configuration where the radiographic marker 100, 200 is positioned down the implant shell midline C1, C2 is that the radiographic marker 100, 200 is able to provide the surgeon with a means for determining if the breast implant is mal-positioned after surgery which is a common issue with shaped breast implants.

The aforementioned features are believed to be advantageous over currently existing radiographic identifiers in that the radiographic identifiers 110 and 210 as oriented on the respective midlines C1 and C2 allow a practitioner to determine with certainty whether the implant has been implanted optimally in the body without being misaligned. That is, prior to the development of the radiographic identifiers 110 and 210 as oriented on the respective midlines C1 and C2 as described herein, movements of the implants during surgery could cause the breast implants to rotate or turn without the practitioner being aware of such adverse configurations after the implantation has been completed. The breast implants, as described herein, therefore allow the practitioner to achieve an advantageous technique by ensuring that the prosthesis implanted by the practitioner is properly configured inside the mammalian body.

Various examples of aspects of the disclosure are described as numbered clauses (1, 2, 3, etc.) for convenience. These are provided as examples and do not limit the subject technology. Identification of the figures and reference numbers are provided below merely as examples for illustrative purposes, and the clauses are not limited by those identifications.

Clause 1: A marker for identifying a characteristic of a breast implant while in vivo, the marker comprising: a first layer incorporating a radiopaque material therein, the first layer comprising an outer surface and an inner surface disposed opposite to the outer surface; and a non-radiopaque second layer coupled to and positioned over the inner surface of the first layer, wherein: the first layer comprises a radiopaque identifier defined thereon by an outline formed from an absence of at least a portion of the radiopaque material to create readable characters which permit the radiopaque identifier to be viewable in vivo when exposed to a radiographic source of energy.

Clause 2: The marker of Clause 1, wherein the first layer is a non-radiopaque layer having the radiopaque material distributed within the non-radiopaque layer.

Clause 3: The marker of any of the preceding Clauses, wherein the radiopaque material comprises a barium sulfate powder or ink distributed within the radiopaque layer.

Clause 4: The marker of any of the preceding Clauses, wherein the first layer is laminated to the non-radiopaque second layer.

Clause 5: The marker of any of the preceding Clauses, wherein at least one of the first layer and the second layer comprises a silicone sheet, and the radiopaque material comprises a strip of barium sulfate.

Clause 6: The marker of any of the preceding Clauses, wherein the readable characters of the radiopaque identifier are formed by laser etching and removal of at least a portion of the radiopaque material.

Clause 7: The marker of any of the preceding Clauses, wherein the radiographic source of energy comprises X-Rays.

Clause 8: A breast implant comprising: a flexible shell having an anterior face including an outer surface and an inner surface; and a marker attached to the inner surface of the anterior face of the shell, the marker including: a first layer of material having a radiopaque surface with readable characters for identifying a characteristic of the breast implant while in vivo, the readable characters defined by at least one void in the material of the radiopaque surface; and a second layer of non-radiopaque material laminated onto the radiopaque surface, wherein the first layer of material with the readable characters is interposed between the inner surface of the anterior face of the shell and the second layer, and the readable characters are viewable in vivo using conventional imaging techniques.

Clause 9: The breast implant of Clause 8, wherein: the anterior face further includes an upper pole region and a lower pole region, and a midline of the flexible shell extends from the upper pole region to the lower pole region; and the marker is positioned on the midline to indicate orientation of the breast implant during surgery.

Clause 10: The breast implant of Clause 9, wherein the marker is shaped as a strip of material positioned along the midline.

Clause 11: The breast implant of any of Clauses 8-10, wherein the first layer is a non-radiopaque layer having the radiopaque surface positioned on or within the non-radiopaque layer.

Clause 12: The breast implant of any of Clauses 8-11, wherein the radiopaque surface comprises a barium sulfate powder or ink.

Clause 13: The breast implant of any of Clauses 8-12, wherein the first layer of material having a radiopaque surface is laminated to the second layer of non-radiopaque material.

Clause 14: The breast implant of any of Clauses 8-13, wherein each of the first layer and the second layer comprises a silicone material, the radiopaque surface comprising barium sulfate material incorporated into the silicone material of the first layer.

Clause 15: The breast implant of any of Clauses 8-14, wherein the shell comprises a silicone elastomeric material.

Clause 16: The breast implant of any of Clauses 8-15, wherein the radiopaque surface comprises a strip of barium sulfate material.

Clause 17: The breast implant of any of Clauses 8-16, wherein the readable characters of the radiopaque surface are formed by laser etching and removal of at least a portion of the radiopaque surface Clause 18: The breast implant of any of Clauses 8-17, wherein the conventional imaging techniques comprise X-Ray imaging.

Clause 19: A method of manufacturing a radiopaque identifier for a breast implant, the method comprising: providing a first layer having a radiopaque material; attaching a second layer of non-radiopaque material to the first layer of material, wherein the radiopaque material is interposed between an outer surface of the first layer and the second layer; and removing at least a portion of material from the radiopaque material to form the radiopaque identifier including readable characters defined by the removed portion of radiopaque material, wherein the readable characters are viewable in vivo using conventional imaging techniques.

Clause 20: The method of Clause 19, wherein the attaching the second layer of non-radiopaque material to the first layer of radiopaque material comprises laminating the second layer of non-radiopaque material to the first layer of radiopaque material.

Clause 21: The method of any of Clauses 19-20, wherein the removing at least a portion of the radiopaque material comprises controllably marking and cutting out the portion of the radiopaque material of the first layer with a laser.

Clause 22: The method of any of Clauses 19-21, wherein providing the first layer of material comprises incorporating barium sulfate into a silicone sheet.

Clause 23: The method of Clause 22, wherein the first layer of material comprises silicone incorporating barium sulfate, and the attaching a second layer of non-radiopaque material comprises attaching a clear silicone sheet to the first layer of silicone incorporating the barium sulfate.

Clause 24: A method of manufacturing a breast implant, comprising: forming a breast implant marker having readable characters for identifying a characteristic of the breast implant while in vivo, the forming comprising: providing a first layer of material having an inner surface and an outer surface with a radiopaque material incorporated between the inner and outer surfaces; attaching a second layer of non-radiopaque material to the inner surface of the first layer of material; and removing at least a portion of the radiopaque material from the first layer of material to form readable characters defined by absence of the portion of radiopaque material; providing a shell having an anterior face; and attaching the breast implant marker to the anterior face of the shell, wherein the first layer of material having the readable characters is interposed between the anterior face of the shell and the second layer of non-radiopaque material, and the readable characters are viewable in vivo using conventional imaging techniques.

Clause 25: The method of Clause 24, wherein the anterior face further includes an upper pole region and a lower pole region, and a midline of the shell extends from the upper pole region to the lower pole region, the method further comprising positioning the marker on the midline to indicate orientation of the breast implant during surgery.

Clause 26: The method of any of Clauses 24-25, wherein the attaching the breast implant marker to the anterior face of the shell comprises attaching the breast implant marker to an inner layer of the anterior face of the shell.

Clause 27: The method of Clause 26, wherein the attaching the marker to the inner surface of the shell comprises silicone vulcanizing the marker to the inner surface of the anterior face of the shell.

Clause 28: The method of any of Clauses 24-27, wherein the attaching the marker to the inner surface of the anterior face of the shell comprises silicone vulcanizing the marker to the inner surface of the anterior face of the shell.

Clause 28: The method of any of Clauses 24-27, wherein the attaching the second layer of non-radiopaque material to the first layer of radiopaque material comprises laminating the second layer of non-radiopaque material to the first layer of radiopaque material.

Clause 29: The method of any of Clauses 24-28, wherein the removing at least a portion of the radiopaque material comprises controllably marking and cutting out the portion of the radiopaque material from the first layer of material with a laser.

Clause 30: The method of any of Clauses 24-29, wherein: the providing a first layer of material comprises incorporating barium sulfate into a silicone sheet; and the attaching a second layer of non-radiopaque material comprises attaching a clear silicone sheet to the silicone sheet having the barium sulfate.

Clause 31: The method of any of Clauses 24-30, wherein the attaching the breast implant marker to the anterior face of the shell comprises attaching the breast implant marker to an outer surface of the anterior face of the shell.

Clause 32: The method of Clause 31, wherein the attaching the marker to the outer surface of the shell comprises silicone vulcanizing the marker to the outer surface of the anterior face of the shell.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A breast implant comprising:
   a flexible shell having an anterior face including an outer surface and an inner surface; and
   a marker attached to the inner surface of the anterior face of the shell, the marker including:
      a first layer of material having a radiopaque surface with readable characters for identifying a characteristic of the breast implant while in vivo, the readable characters defined by an outline formed from an absence of at least a portion of material of the radiopaque surface; and
      a second layer of non-radiopaque material laminated onto the inner surface and tapered around the radiopaque surface,
   wherein the first layer of material with the readable characters is interposed between the inner surface of the anterior face of the shell and the second layer, and the readable characters are viewable in vivo using conventional imaging techniques.

2. The breast implant of claim 1, wherein:
   the anterior face further includes an upper pole region and a lower pole region, and a midline of the flexible shell extends from the upper pole region to the lower pole region; and
   the marker is positioned on the midline to indicate orientation of the breast implant during surgery.

3. The breast implant of claim 2, wherein the marker is shaped as a strip of material positioned along the midline to indicate proper orientation of the breast implant.

4. The breast implant of claim 1, wherein the first layer is a non-radiopaque layer having the radiopaque surface positioned on or within the non-radiopaque layer.

5. The breast implant of claim 1, wherein the radiopaque surface comprises a barium sulfate powder or ink.

6. The breast implant of claim 1, wherein the first layer of material having a radiopaque surface is laminated to the second layer of non-radiopaque material.

7. The breast implant of claim 1, wherein each of the first layer and the second layer comprises a silicone material, the radiopaque surface comprising barium sulfate material incorporated into the silicone material of the first layer.

8. The breast implant of claim 1, wherein the radiopaque surface comprises a strip of barium sulfate material.

9. The breast implant of claim 1, wherein the readable characters of the radiopaque surface are formed by laser etching and removal of at least a portion of the radiopaque surface.

10. The breast implant of claim 1, wherein the conventional imaging techniques comprise X-Ray imaging.

11. The breast implant of claim 1, wherein the second layer tapers toward the inner layer of the shell of the breast implant.

12. A breast implant comprising:
a flexible shell having an anterior face including an outer surface and an inner surface; and
a radiopaque marker coupled to the inner surface of the anterior face of the shell, the marker comprising first and second layers, the first layer having a radiopaque surface with characters viewable in vivo using conventional imaging techniques for identifying a characteristic of the breast implant, the second layer having a silicone material coupled to the inner surface with the first layer interposed therebetween, the second layer having a perimeter that tapers around the first layer.

13. The breast implant of claim 12, wherein the second layer tapers toward the inner layer of the shell.

14. The breast implant of claim 12, wherein:
the anterior face further includes an upper pole region and a lower pole region, and a midline of the flexible shell extends from the upper pole region to the lower pole region; and
the marker is positioned on the midline to indicate orientation of the breast implant during surgery.

15. The breast implant of claim 12, wherein the marker is shaped as a strip of material positioned along a midline of the shell to indicate proper orientation of the breast implant.

16. The breast implant of claim 12, wherein the first layer is a non-radiopaque layer having the radiopaque surface positioned on or within the non-radiopaque layer.

17. The breast implant of claim 12, wherein the radiopaque surface comprises a barium sulfate powder or ink.

18. The breast implant of claim 12, wherein the second layer is laminated onto the inner surface.

19. The breast implant of claim 12, wherein each of the first layer and the second layer comprises a silicone material, the radiopaque surface comprising barium sulfate material incorporated into the silicone material of the first layer.

20. The breast implant of claim 12, wherein the radiopaque surface comprises a strip of barium sulfate material.

21. The breast implant of claim 12, wherein the readable characters are defined by an outline formed from an absence of at least a portion of material of the radiopaque surface.

22. The breast implant of claim 12, wherein the readable characters are formed by laser etching and removal of at least a portion of the radiopaque surface.

* * * * *